(12) United States Patent
Calderon-Colon et al.

(10) Patent No.: US 10,842,890 B2
(45) Date of Patent: Nov. 24, 2020

(54) CONTRAST AGENT AND ASSOCIATED METHODS

(71) Applicant: The Johns Hopkins University, Baltimore, MD (US)

(72) Inventors: Xiomara Calderon-Colon, Laurel, MD (US); George L. Coles, Jr., Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 582 days.

(21) Appl. No.: 15/383,709

(22) Filed: Dec. 19, 2016

(65) Prior Publication Data
US 2018/0169276 A1 Jun. 21, 2018

(51) Int. Cl.
*A61K 49/22* (2006.01)

(52) U.S. Cl.
CPC .................. *A61K 49/223* (2013.01)

(58) Field of Classification Search
None
See application file for complete search history.

(56) References Cited

U.S. PATENT DOCUMENTS

| | | | | |
|---|---|---|---|---|
| 5,976,501 A | * | 11/1999 | Jablonski | A61K 49/223 424/9.52 |
| 2007/0116848 A1 | * | 5/2007 | Aldred | A23C 9/1544 426/564 |
| 2008/0213453 A1 | * | 9/2008 | Burmester | A23C 9/1524 426/565 |
| 2013/0303631 A1 | * | 11/2013 | Quan | A61K 8/645 514/773 |
| 2015/0273407 A1 | * | 10/2015 | Gil | C07K 14/37 210/650 |

FOREIGN PATENT DOCUMENTS

WO WO-2014144364 A1 * 9/2014 ........... A61K 9/5031

* cited by examiner

*Primary Examiner* — Jennifer Lamberski
(74) *Attorney, Agent, or Firm* — Sung T. Kim

(57) ABSTRACT

Example substances and methods relating to contrast agents are provided. An example method includes combining a surface active protein, a stabilizer, and a dispersion media to form a solution. The example method may further include aerating the solution in a gas to form a contrast agent comprising at least one microbubble formed from an interaction between the surface active protein and the stabilizer. A diameter of the at least one microbubble may be proportional to a pressure of an external environment of the contrast agent, such that measurement of the diameter may allow for measurement of the pressure.

17 Claims, 4 Drawing Sheets

```
                          ┌─────────────────────────────┐
                          │  Provide a hydrophobin protein │──── 410
                          └──────────────┬──────────────┘
                                         ▼
                          ┌─────────────────────────────┐
                          │      Provide a stabilizer      │──── 420
                          └──────────────┬──────────────┘
                                         ▼
                          ┌─────────────────────────────┐
                          │    Provide a dispersion media  │──── 430
                          └──────────────┬──────────────┘
                                         ▼
                          ┌─────────────────────────────┐
                          │ Combine the hydrophobin protein,│
                          │ the stabilizer, and the dispersion│──── 440
                          │     media to form a solution    │
                          └──────────────┬──────────────┘
                                         ▼
                          ┌─────────────────────────────┐
                          │         Provide a gas          │──── 450
                          └──────────────┬──────────────┘
                                         ▼
                          ┌─────────────────────────────┐
                          │ Aerate the solution to form a  │
                          │ contrast agent comprising a    │──── 460
                          │    plurality of microbubbles   │
                          └─────────────────────────────┘
```

FIG. 4

CONTRAST AGENT AND ASSOCIATED METHODS

TECHNICAL FIELD

Exemplary embodiments described herein generally relate to the generation of substances in the form of contrast agents that can be leveraged to measure pressures internal to a body.

BACKGROUND

There are numerous applications where measuring the pressure inside of a cavity may be helpful. However, measuring internal pressures can often times be difficult to accomplish because accessing the cavity is difficult or impossible. For example, in order to properly treat some brain conditions, careful monitoring of the pressure of the cerebrospinal fluid in the cranial cavity is required. Conventional techniques often require invasive procedures to take simple pressure measurements. In some instances, a contrast agent is utilized in association with ultrasound technology to measure internal pressures. However, conventional contrast agents degrade quickly over time, and therefore invasive procedures to introduce the contrast agent to the body are required for each pressure measurement occasion.

BRIEF SUMMARY OF SOME EXAMPLES

Example substances and methods relating to contrast agents are provided. According to one example embodiment, an example method is provided. The example method may comprise combining a surface active protein, a stabilizer, and a dispersion media to form a solution. The example method may further comprise aerating the solution with a gas at a predetermined mixing speed to form a contrast agent comprising a microbubble formed from an interaction between the surface active protein and the stabilizer. The microbubble may have a shell that encapsulates the gas, and the microbubble may be disposed within the dispersion media. Further, the dispersion media may provide structural support to the shell of the microbubble and a diameter of the microbubble may be proportional to a pressure of an external environment of the contrast agent.

According to another example embodiment, an example contrast agent substance is provided. The example contrast agent may comprise a plurality of microbubbles, and each microbubble may have a shell that encapsulates a gas. The microbubbles may be formed via aeration of a surface active protein with a stabilizer. The example contrast agent may further comprise a dispersion media. The microbubbles may be disposed within the dispersion media, and the dispersion media may provide structural support to the shells of the microbubbles. A diameter of at least one microbubble may be proportional to a pressure of the external environment of the contrast agent.

According to another example embodiment, an example article of manufacture is provided. The example article of manufacture may comprise a plurality of microbubbles, and each microbubble may have a shell that encapsulates a gas. The microbubbles may be formed via aeration of a class II hydrophobin protein with a stabilizer. The example article of manufacture may further comprise a dispersion media. The microbubbles may be disposed within the dispersion media, and the dispersion media may provide structural support to the shells of the microbubbles. A diameter of at least one microbubble may be proportional to a pressure of the external environment of the contrast agent.

BRIEF DESCRIPTION OF THE SEVERAL VIEWS OF THE DRAWING(S)

Having thus described some example embodiments in general terms, reference will now be made to the accompanying drawings, which are not necessarily drawn to scale, and wherein:

FIG. 4 illustrates a flowchart of an example method for manufacturing a contrast agent according to some example embodiments.

DETAILED DESCRIPTION

Figure 1:
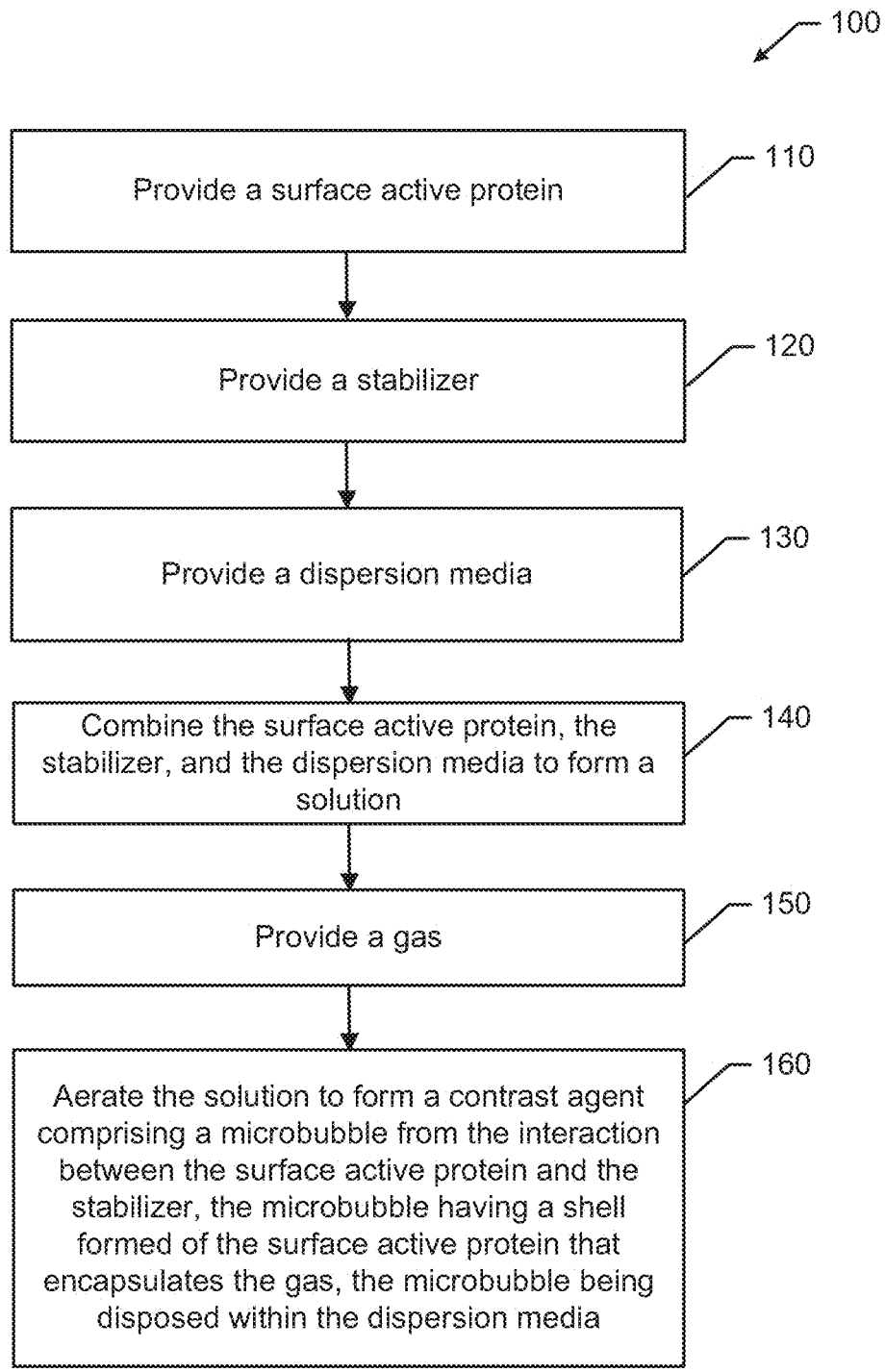
FIG. 1 illustrates a flowchart of an example method associated with creating and utilizing a contrast agent according to some example embodiments.

Some example embodiments now will be described more fully hereinafter with reference to the accompanying drawings, in which some, but not all example embodiments are shown. Indeed, the examples described and pictured herein should not be construed as being limiting as to the scope, applicability, or configuration. Rather, these example embodiments are provided to satisfy applicable legal requirements. Like reference numerals refer to like elements throughout. Furthermore, as used herein, the term "or" is to be interpreted as a logical operator that results in true whenever one or more of its operands are true. The term "providing" is to be interpreted as making an object available for further interaction.

Example embodiments described herein relate to the formation and utilization of a contrast agent that may be used with ultrasound techniques to, for example, measure pressures internal to a cavity (e.g., of the human body). Accordingly, some example embodiments in the form of a contrast agent can be utilized as an ultrasound contrast medium for medical sonography. In this regard, an ultrasound contrast agent comprising microbubbles with an increased foam stability may be generated, where the shells of the microbubbles operate to reflect or echo sound waves off of their surfaces. Further, the microbubbles of the contrast agent can resonant in response to a driving pressure pulse transmitted by the ultrasound system. The reflected or echoed sound waves can be analyzed to determine an environmental pressure being applied to the contrast agent.

Contrast-enhanced ultrasound techniques leverage the structure and size of microbubbles in a contrast agent. Conventional contrast agents that employ microbubbles often suffer from the structure and size of the microbubbles decaying over time, and therefore reliable measurements cannot be taken shortly after the contrast agent has been introduced to the target environment. Because of this decaying characteristic of conventional contrast agent microbubbles, contrast agent material must be reintroduced (e.g., injected) into the environment of interest (e.g., the cranial cavity) before each measurement procedure, which can be invasive in medical applications. However, the example contrast agents described herein include microbubbles that maintain their structure and size for longer durations (e.g., weeks or months). Therefore, multiple measurement procedures may be performed over time without having to reintroduce additional contrast agent to the environment of interest and without the invasive procedures required to do so. Further, because the microbubbles may have a longer useful life, different delivery systems may be utilized, including but not limited to, therapeutic delivery.

As further described herein, some example embodiments are directed to the formation of a contrast agent having a high foam stability and comprised of microbubbles formed by surface active proteins, such as class II hydrophobins (HFBII). The microbubbles in an example contrast agent may be formed via aeration of the surface active protein with a stabilizer and disposed within a dispersion media, such as water or other aqueous solution.

In this regard, FIG. 1 shows a flowchart of an example method 100 for forming and using a contrast agent according to some example embodiments. The example method 100 includes providing a surface active protein at 110. The surface active protein may be a type of biopolymer, which includes proteins, that has a relatively high elasticity and high viscosity. Further, the surface active protein may be a substance that operates as a foaming agent. The surface active protein may be provided at a given concentration, such as, for example, 0.05, 0.1, or 0.3 percent by weight.

According to some example embodiments, the surface active protein may be an amino acid that is able to form structured films and membranes, for example, via self-assembly and surfactant properties. Further, according to some example embodiments, the surface active protein may have a four-disulfide bridge structure and an amphipathic tertiary structure. Examples of such proteins include hydrophobins and, in particular, class II hydrophobins, which are a consumable protein that can be extracted from fungi. Hydrophobins are small proteins (7-9 kilodaltons) that are capable of self-assembly at a hydrophobic/hydrophilic interface. As exemplified by hydrophobins, the surface active protein may also form a hydrophobic coating that can operate to repel, for example, water.

At 120 of FIG. 1, the example method may further comprise providing a stabilizer. The stabilizer may be a substance that will interact with the surface active protein to form microbubbles. According to some example embodiments, the stabilizer may be a polysaccharide, such as xanthan or xanthan gum. In example embodiments using xanthan, concentrations such as, for example, 0.05, 0.01, and 0.1 percent by weight may be used.

At 130, the example method may include providing a dispersion media. The dispersion media may be water or other aqueous solution as described above. However, according to some example embodiments, the dispersion media may be an aqueous solution of dextran, gelatin, collagen, alginic acid sodium salt, or bovine serum albumin. According to some example embodiments, the dispersion media may be a biomaterial.

At 140, the surface active protein, the stabilizer, and the dispersion media may be combined to form a solution. The surface active protein, stabilizer, and the dispersion media may be combined in any order and generally in any manner prior to the aeration operation at 160, described in more detail below. According to some example embodiments, combining the surface active protein, the stabilizer, and the dispersion media may occur in parallel or at the same time as the aeration operation at 160. Further, the surface active protein and the dispersion media may be combined in advance of adding the stabilizer according to some example embodiments.

Further, at 150, a gas may be provided that may assist in the aeration operation to create microbubbles that encapsulate the gas. According to some example embodiments, the gas may include, for example, oxygen, nitrogen, a combination of oxygen and nitrogen, or the like.

At 160, aeration of the solution to form a contrast agent may be performed. The contrast agent may include at least one, and likely a plurality of, microbubbles. The microbubbles may be formed by the interaction between the surface active protein and the stabilizer due to the mixing caused by the aeration. According to some example embodiments, a predetermined mixing speed may be utilized for aeration, such as, for example, 6,000 rotations per minute (rpms) or 12,000 rpms.

Figure 2:
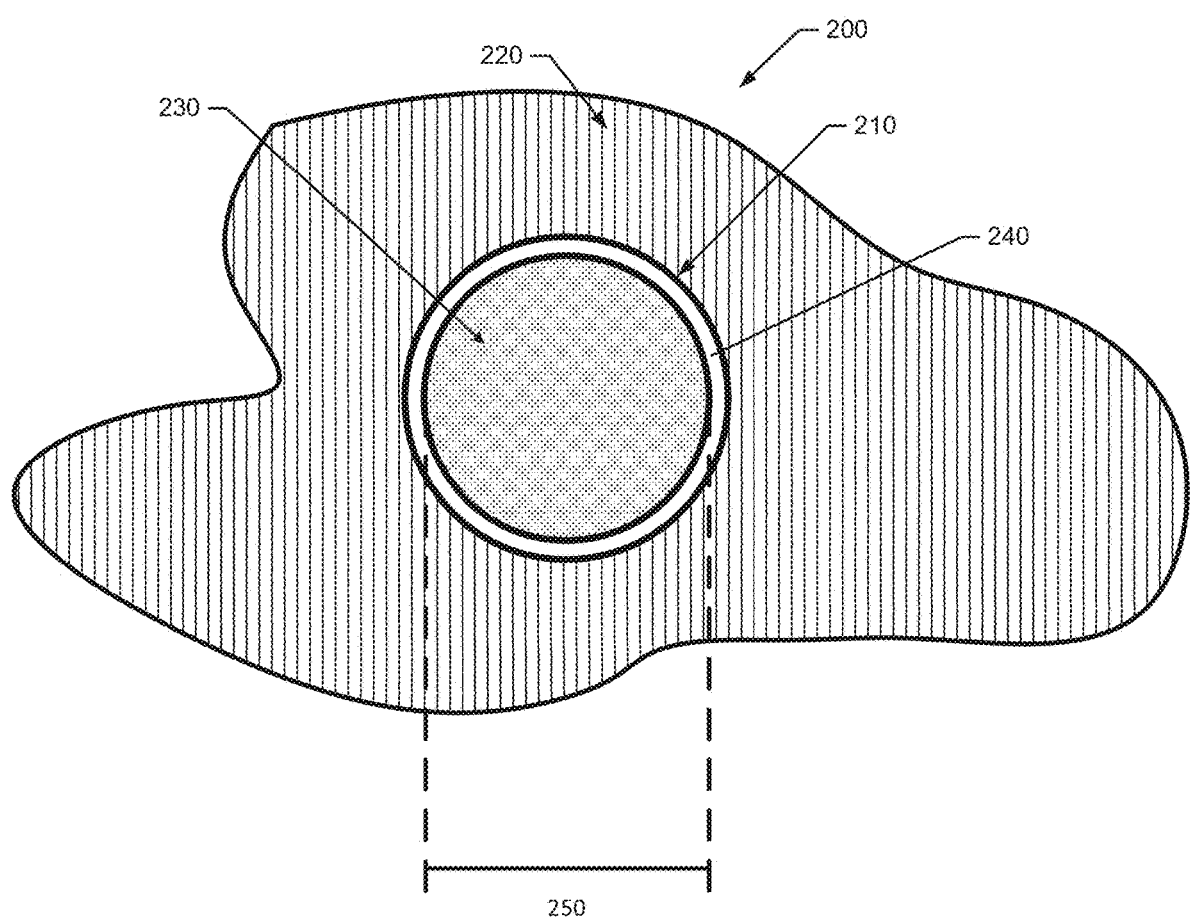
FIG. 2 illustrates a contrast agent and, in particular, a microbubble in a dispersion media according to some example embodiments.

Referring to FIG. 2, the aeration at 160 may form the microbubble 210 of the contrast agent 200. In this regard, the microbubble 210 may have a shell 240 that is formed from the interaction between the surface active protein and the stabilizer to encapsulate the gas 230. Further, the microbubble 210 may be disposed within the dispersion media 220. According to some example embodiments, the presence of the dispersion media 220 may operate to provide additional support to the mechanical structure of the microbubble 210 and the shell 240 to increase the longevity of the microbubble 210 at a desired size. The additional structural support provided by the dispersion media 220 may result from the density of the dispersion media itself and/or from the combination of the dispersion media 220 with a cross-link reaction involving the surface active protein, which may form covalent bonds between the shell 240 and the dispersion media 220. Further, the microbubble 210 may have a generally spherical shape and have a diameter 250. The microbubble 210 may be formed to have a desired diameter 250 based on, for example, the concentration of surface active protein, the concentration of the stabilizer, and the aeration mixing speed. For example, Table 1 shown below lists combinations of various concentrations and mixing speeds that have been tested to obtain microbubbles having the different diameters:

TABLE 1

Microbubble Approximate Diameters

| Concentration of Class II Hydrophobin (% weight) | Concentration of xanthan (% weight) | Aeration Mixing Speed (rpm) | Microbubble Diameter (μm) |
| --- | --- | --- | --- |
| 0.05 | 0.05 | 6,000 | 100 |
| 0.1 | 0.1 | 6,000 | 100 |
| 0.3 | 0.1 | 6,000 | 100 |
| 0.05 | 0.1 | 12,000 | 200 |
| 0.1 | 0.05 | 12,000 | 100 |
| 0.3 | 0.01 | 12,000 | 100 |

In addition to the diameter of the microbubbles, other aspects of the microbubbles may be affected by differences in the concentrations and aeration mixing speed. For example, different thicknesses of the shells of the microbubbles may be formed. Further, the density of microbubbles in the dispersion media and the uniformity of microbubbles per unit volume of contrast agent may be controlled. Additionally, the frequency at which the microbubbles will burst may be controlled using these factors.

Microbubbles formed into the contrast agent may change in size (i.e., diameter) based on changes in the pressure exerted on the microbubbles by the surrounding environment (e.g., a cavity of the human body). In this regard, increases in pressure may cause the diameter of a microbubble to decrease, and decreases in pressure may cause the microbubble's diameter to increase. As such, when the sound beam of an ultrasound device is directed towards the contrast agent, the sound reflections from microbubbles in the contrast agent may be a function of microbubble diameter, which may be analyzed to measure pressure in the surrounding environment. In this regard, the diameter of the microbubble may be proportional to the pressure being exerted on the microbubble by the surrounding environment. Moreover, microbubbles located in different regions of the surrounding environment may exhibit different diameters, which may correspond to differing pressures between the regions.

According to some example embodiments, the example method may further include a cross-link reaction. The cross-link reaction may occur after or during the aeration at 160. In this regard, a cross-link reaction may occur between the surface active protein (e.g., hydrophobin), the stabilizer (e.g., xanthan), and a cross-link substance (also referred to as a cross-linker) to chemically cross-link the molecules. The cross-linker may be a photoinitiator. Examples of cross-linkers that may be utilized in the example method include, but are not limited to, 2,2-dimethoxy-2-phenylacetophenone, and 2-hydroxy-4'-(2-hydroxyethoxy)-2-methylpropiophenone (Irgacure 2959). Another example cross-linker that has been used in natural, unmodified materials and mixtures is EDC (N-(3-Dimethylaminopropyl)-N-ethylcarbodiimide)/NHS (N-Hydroxysuccinimide), which may operate to couple amines and carboxylic acid groups or carboxylic acid groups together. The cross-link reaction may include exposing the microbubbles to an ultraviolet light to activate a cross-linker that is in the form of a photoinitiator. Alternatively, in examples where non-photoinitiators are used as cross-linkers, a different activation technique may be used, such as, for example, the addition of a catalyst. The sites for cross-linking between the surface active protein and the cross-link substance may be lysine, histidine, cysteine, and tysine. Examples of cross-link substances that may be used to cause a cross-link reaction include 1-ethyl-3-(3 dimethyl-aminopropyl)-1-carbodiimide hydrochloride (EDC), N-hydroxysuccinimide (NHS), glutaraldehyde, or 2-hydroxy-4'-2(2-hydroxyethoxy)-2-methylpropiophenone (Irgacure 2959).

Further, according to some example embodiments, pressure measurements may be taken using the contrast agent. In this regard, the example method may include measuring the pressure of an environment external to the contrast agent via ultrasound. The ultrasound reflection or echo may have an amplitude that is linearly related to a pressure applied to the microbubbles. The range of pressures for measurement may be 0 to 30 mmHg. According to some example embodiments, the example method may further include disposing the contrast agent in a sealed container prior to measuring the pressure. In this regard, with reference to FIG. 3, an apparatus 300 is shown that includes a contrast agent container 310. The contrast agent container 310 may house the contrast agent 320, which may comprise microbubbles 330 and dispersion media 340, as provided herein. The contrast agent container 310, which may be in the form of tube, may be hermetically sealed to facilitate placement within a body cavity, such as, for example, the cranial cavity to measure cerebrospinal fluid pressure. The contrast agent container 310 may be sealed under atmospheric pressure or a slightly higher pressure using the same gas that is encapsulated by the microbubbles. The contrast agent container 310 may be constructed such that changes in the pressure applied to the container 310 may be translated into the contrast agent 320 and, in turn, to the microbubbles 330. Accordingly, the pressures measured with respect to the microbubbles 330 would be representative of the external pressure exerted on the contrast agent container 310. Further, the contrast agent container 310 may operate to provide further support to the microbubbles 330 to extend the duration that the microbubbles 330 maintain their structure and size.

Figure 3:
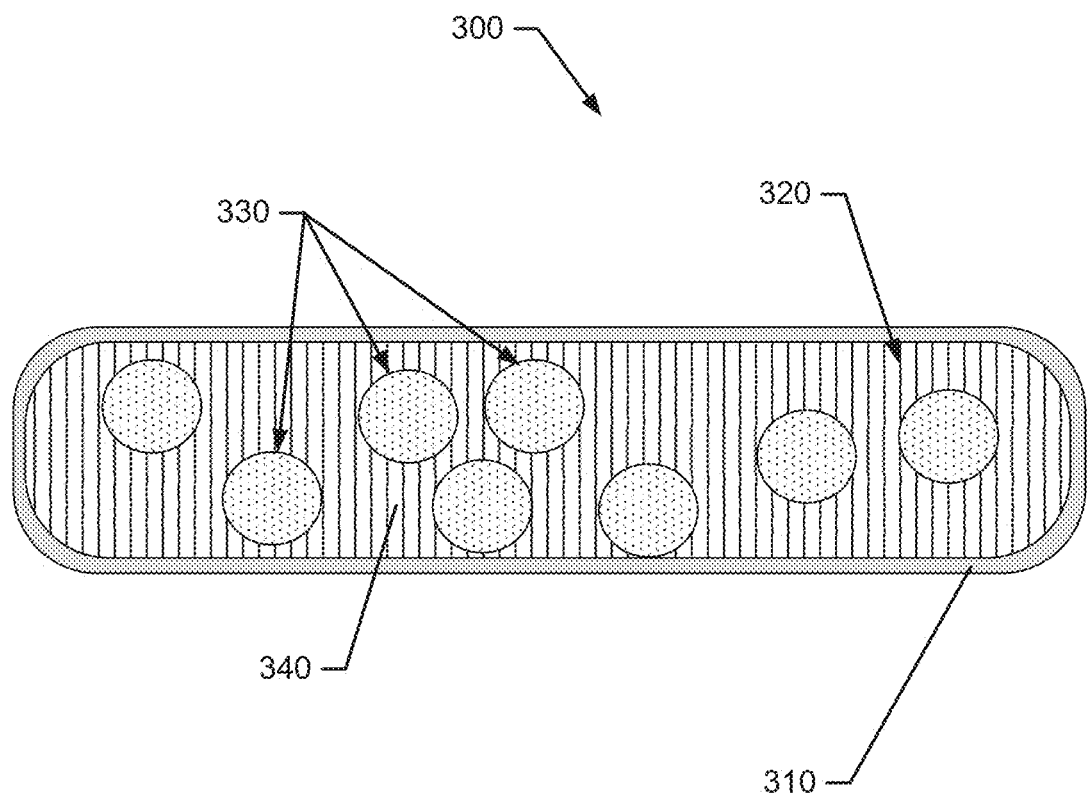
FIG. 3 illustrates a contrast agent in a container according to some example embodiments.

In view of the description provided herein, particularly with respect to FIGS. 2 and 3, an example substance in the form of a contrast agent is provided. The contrast agent may comprise a plurality of microbubbles. Each microbubble may have a shell that encapsulates a gas. The microbubbles may be formed via aeration of a surface active protein with a stabilizer. Further, the contrast agent may comprise a dispersion media, where the microbubbles are disposed within the dispersion media. The dispersion media may provide structural support to the shells of the microbubbles. Additionally, a diameter of at least one of the microbubbles may be proportional to a pressure of the external environment of the contrast agent exerted on the microbubbles, such that measurement of the diameter may allow for measurement of the pressure.

According to some example embodiments, the surface active protein may exhibit a disulfide bridge structure and the surface active protein may comprise a hydrophobin. The stabilizer may comprise xanthan. Further, the plurality of microbubbles may be formed via a cross-link reaction between the surface active protein, the stabilizer, and a cross-link substance. According to some example embodiments, the dispersion media may comprise at least one of dextran, gelatin, collagen, alginic acid sodium salt, or bovine serum albumin.

Based on the foregoing and as further described herein, another example method is provided. With respect to FIG. 4, an example method 400 of manufacturing a contrast agent is provided. In this regard, the example method 400 may include providing a hydrophobin protein at 410. The hydrophobin protein may be a class II hydrophobin. Further, at 420, a stabilizer may be provided, and at 430, a dispersion media may be provided. The hydrophobin protein, the stabilizer, and the dispersion media may be combined to form a solution at 440. Further, at 450, a gas may be provided, and aeration of the solution with the gas may be performed at 460. Aeration at 460 may form a contrast agent comprising a plurality of microbubbles. Each microbubble in the plurality of microbubbles may have a shell that encapsulates the gas. The diameter of at least one of the microbubbles within the plurality of microbubbles may be proportional to a pressure of an external environment of the contrast agent.

According to some example embodiments, the stabilizer of the method 400 may comprise xanthan. Further, according to some example embodiments, the example method 400 may further include causing a cross-link reaction between the hydrophobin protein, the stabilizer, the dispersion media, and a cross-link substance. The dispersion media may comprise a biomaterial, such as, for example, dextran, gelatin, collagen, alginic acid sodium salt, or bovine serum albumin.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe exemplary embodiments in the context of certain exemplary combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. In cases where advantages, benefits or solutions to problems are described herein, it should be appreciated that such advantages, benefits and/or solutions may be applicable to some example embodiments, but not necessarily all example embodiments. Thus, any advantages, benefits or solutions described herein should not be thought of as being critical, required or essential to all embodiments or to that which is claimed herein. Although specific terms are employed herein, they are used in a generic and descriptive sense only and not for purposes of limitation.

That which is claimed:

1. A method comprising:

combining a surface active protein, a stabilizer, and a dispersion media to form a solution; and aerating the solution with a gas at a predetermined mixing speed and chemically cross-linking the surface active protein and the stabilizer with a cross-link substance after or during the aerating to form a contrast agent comprising a microbubble formed from an interaction between the surface active protein and the stabilizer, the microbubble having a crosslinked shell that encapsulates the gas, the microbubble being disposed within the dispersion media;

wherein the surface active protein comprises a hydrophobin, wherein the stabilizer comprises a polysaccharide, wherein the dispersion media provides structural support to the crosslinked shell of the microbubble, and wherein a diameter of the microbubble is proportional to a pressure applied to the contrast agent.

2. The method of claim 1, wherein the surface active protein is structured to exhibit a disulfide bridge structure.

3. The method of claim 1, wherein the hydrophobin comprises a class II hydrophobin.

4. The method of claim 1, wherein the polysaccharide comprises xanthan or xanthan gum.

5. The method of claim 1, wherein the dispersion media comprises at least one of dextran, gelatin, collagen, alginic acid sodium salt, or bovine serum albumin.

6. The method of claim 1, wherein the polysaccharide comprises xanthan, and the dispersion media comprises a biomaterial.

7. The method of claim 1, further comprising measuring the pressure applied to the contrast agent via ultrasound.

8. The method of claim 7, further comprising disposing the contrast agent in a sealed container prior to measuring the pressure applied to the contrast agent.

9. A contrast agent comprising:

a plurality of microbubbles, each microbubble having a crosslinked shell and encapsulating a gas, the microbubbles being formed via aeration of a surface active protein with a stabilizer and a chemical cross-link reaction between the surface active protein and the stabilizer with a cross-link substance after or during the aeration, the surface active protein comprising a hydrophobin and the stabilizer comprising a polysaccharide; and a dispersion media, the microbubbles being disposed within the dispersion media and the dispersion media providing structural support to the crosslinked shells of the microbubbles;

wherein a diameter of at least one microbubble is proportional to a pressure applied to the contrast agent.

10. The contrast agent of claim 9, wherein the surface active protein exhibits a disulfide bridge structure.

11. The contrast agent of claim 9, wherein the hydrophobin comprises a class II hydrophobin.

12. The contrast agent of claim 9, wherein the polysaccharide comprises xanthan or xanthan gum.

13. The contrast agent of claim 9, wherein the dispersion media comprises at least one of dextran, gelatin, collagen, alginic acid sodium salt, or bovine serum albumin.

14. An article of manufacture comprising:

a plurality of microbubbles, each microbubble having a crosslinked shell and encapsulating a gas, the microbubbles being formed via aeration of a class II hydrophobin with a stabilizer and a chemical cross-link reaction between the class II hydrophobin and the stabilizer with a cross-link substance after or during the aeration, the stabilizer comprising a polysaccharide; and a dispersion media, the microbubbles being disposed within the dispersion media and the dispersion media providing structural support to the crosslinked shells of the microbubbles;

wherein a diameter of at least one microbubble is proportional to a pressure applied to the at least one microbubble.

15. The article of manufacture of claim 14, wherein the polysaccharide comprises xanthan or xanthan gum.

16. The article of manufacture of claim 14, wherein the dispersion media comprises at least one of dextran, gelatin, collagen, alginic acid sodium salt, or bovine serum albumin.

17. The article of manufacture of claim 14, further comprising a hermetically sealed container, the hermetically sealed container having the plurality of microbubbles and the dispersion media disposed therein.

* * * * *